(12) United States Patent  (10) Patent No.: US 10,098,711 B2
Yousefian  (45) Date of Patent: Oct. 16, 2018

(54) DUAL EXPANDING MANDIBULAR DISTRACTOR

(71) Applicant: Joseph Yousefian, Bellevue, WA (US)

(72) Inventor: Joseph Yousefian, Bellevue, WA (US)

( * ) Notice: Subject to any disclaimer, the term of this patent is extended or adjusted under 35 U.S.C. 154(b) by 0 days.

(21) Appl. No.: 15/076,471

(22) Filed: Mar. 21, 2016

(65) Prior Publication Data

US 2016/0270884 A1  Sep. 22, 2016

Related U.S. Application Data

(60) Provisional application No. 62/135,479, filed on Mar. 19, 2015.

(51) Int. Cl.
*A61C 7/10* (2006.01)
*A61C 7/18* (2006.01)
*A61C 7/16* (2006.01)

(52) U.S. Cl.
CPC .............. *A61C 7/10* (2013.01); *A61C 7/16* (2013.01); *A61C 7/18* (2013.01)

(58) Field of Classification Search
CPC ............... A61C 7/10; A61C 7/16; A61C 7/18
USPC ........................................ 433/7, 24
See application file for complete search history.

(56) References Cited

U.S. PATENT DOCUMENTS

| | | | |
|---|---|---|---|
| 3,977,082 A * | 8/1976 | Siatkowski | A61C 7/10 433/7 |
| 4,144,642 A * | 3/1979 | Wallshein | A61C 7/30 433/11 |
| 4,348,179 A | 9/1982 | Nardella | |
| 5,002,485 A * | 3/1991 | Aagesen | A61C 7/10 433/18 |
| 5,439,377 A * | 8/1995 | Milanovich | A61C 7/10 433/7 |
| 5,564,920 A * | 10/1996 | Klapper | A61C 7/10 433/7 |
| 5,622,493 A * | 4/1997 | Razdolsky | A61B 17/663 433/18 |
| 5,645,422 A * | 7/1997 | Williams | A61C 7/10 433/7 |
| 5,775,907 A * | 7/1998 | Razdolsky | A61B 17/663 128/898 |
| 5,829,971 A * | 11/1998 | Razdolsky | A61B 17/663 433/7 |
| 6,109,916 A * | 8/2000 | Wilcko | A61C 7/00 433/24 |
| 6,220,856 B1 * | 4/2001 | Carano | A61C 7/10 433/7 |

(Continued)

*Primary Examiner* — Nicholas Lucchesi
(74) *Attorney, Agent, or Firm* — Timothy E. Siegel Patent Law, PLLC; Timothy E. Siegel

(57) ABSTRACT

An orthodontic screw system includes two rods connected to rotatable head members. The two rods are couplable to one or more of lower teeth or mandibular bones of a patient. The rotatable head members have threaded holes and pairs of the rotatable head members have opposite hand threads. The screw system also includes two twin screws that have threaded ends of opposite hand threads. Each of the two twin screws is engaged to threads of a pair of the rotatable head members. Rotation of one of the twin screws causes the pair of rotatable head members and the ends of the rods to either move together or move apart. The two twin screws are independently rotatable to cause independent expansion or contraction of different portions of the screw system.

7 Claims, 11 Drawing Sheets

(56) References Cited

U.S. PATENT DOCUMENTS

| | | | | |
|---|---|---|---|---|
| 6,299,439 | B1* | 10/2001 | Kooiman | A61C 7/10 433/7 |
| 6,302,687 | B1* | 10/2001 | King | A61B 17/663 433/18 |
| 6,358,255 | B1* | 3/2002 | Testa | A61B 17/663 433/7 |
| 7,331,781 | B1* | 2/2008 | Bandeen | A61C 7/10 433/7 |
| 2003/0050641 | A1* | 3/2003 | Mommaerts | A61B 17/663 606/71 |
| 2007/0218416 | A1* | 9/2007 | Keles | A61C 7/10 433/7 |
| 2012/0277749 | A1* | 11/2012 | Mootien | A61B 17/663 606/70 |
| 2013/0252195 | A1* | 9/2013 | Popat | A61C 7/10 433/24 |
| 2014/0186788 | A1* | 7/2014 | Sheibani Nia | A61C 7/18 433/7 |
| 2015/0231179 | A1* | 8/2015 | Sahin | A61C 7/10 433/24 |

* cited by examiner

DUAL EXPANDING MANDIBULAR DISTRACTOR

CROSS-REFERENCE TO RELATED APPLICATION

This application claims the benefit of U.S. Provisional Patent Application No. 62/135,479, filed Mar. 19, 2015, which is incorporated herein by reference in its entirety.

BACKGROUND

Orthodontists and dental researchers are constantly searching for new and improved ways to correct the problem of lower jaw constriction with collapsed dental arch or overly wide lower jaw and dental arch causing buccal cross bites.

Lower jaw constriction with collapsed dental arch and crowded dentition are the most common dental malocclusion in young or adult patients due to various etiologies. Transverse mandibular deficiency with crowding of the mandibular anterior teeth is frequently present in patients with Class I and II malocclusions. The condition due to insufficient mandibular arch width in various dimensions can cause further skeletal growth problems if left untreated. This anatomical anomaly can also contribute to the development of upper airway constriction and sleep disordered breathing by impacting the airway during the sleep. The overgrown width of the lower jaw also causing buccal cross bite can cause significant damage to the dentition and growth of the temporomandibular joints.

Mandibular symphysis or line of junction of the two pieces of which the bone is composed at an early period of life fuses by 7-8 months of age, with a range from 6 to 9 months.

SUMMARY

Embodiments of expander devices described herein provide improved orthodontic appliances and protocol for expanding or contracting the jaws and dental arches as well as enlarging the upper pharyngeal airway.

This expander design gives the clinician the ability to direct expansion or constriction forces to various segments of the mandibular arch in nonparallel configuration.

In some embodiments described herein, expander devices provide an arch spreading or contracting device and protocol that is simple in structure and use, that avoids the defects and insufficiencies of the presently available devices, and that, at the same time, is capable of differential nonparallel expansion or contraction of the jaws and dental arches.

In some embodiments described herein, expander devices provide a jaw and dental arch spreading capability that not only addresses the dentition and the jaw bones but also reshapes and expands the oral cavity, behind the soft palate (retropalatal), behind the tongue (retroglossal), and below the tongue (hypoglossal). This can be accomplished by enlarging the mouth and accommodating the position of the tongue forward out of the pharynx, enlarging the airway behind the palate (retropalatal), behind the tongue (retroglossal) and below and behind the tongue (hypoglossal). This will contribute in enlarging the oropharyngeal airway by expanding the environment of the upper airway starting from retropalatal area, retroglossal area, and hypoglossal area.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
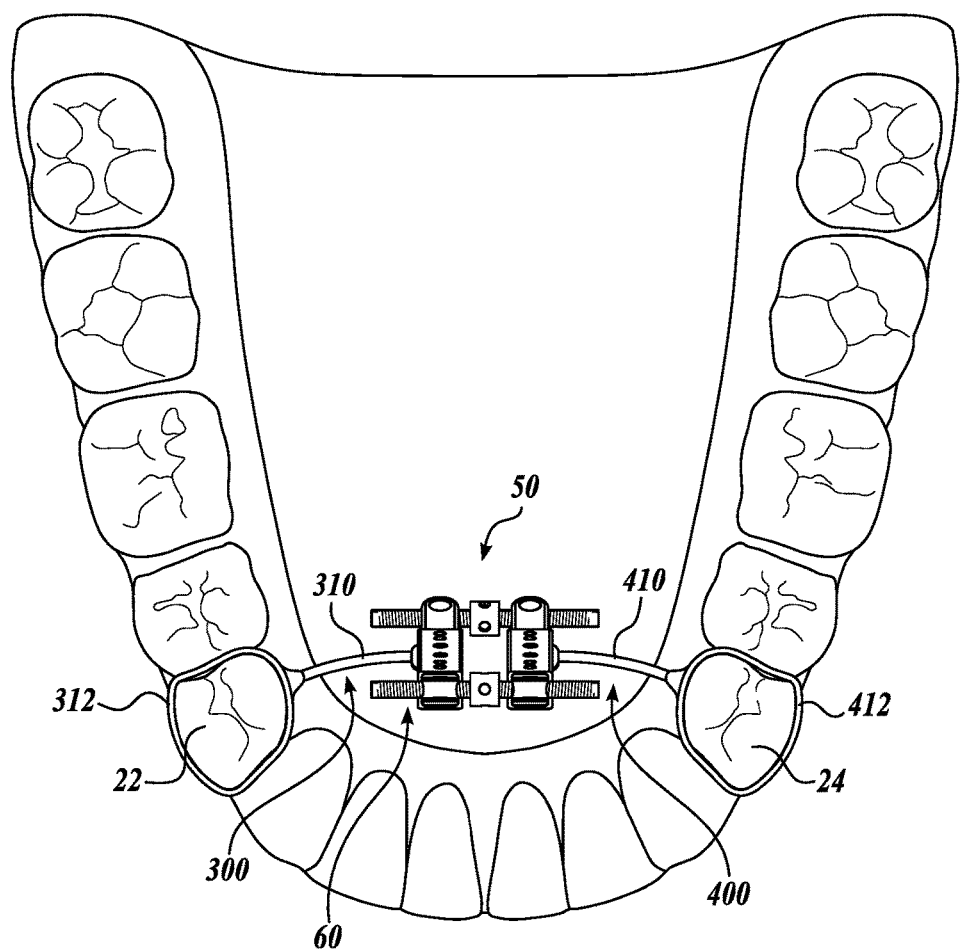
FIG. 1 shows a top view of a mandibular distractor according to a first representative embodiment of the present disclosure, wherein the mandibular distractor is installed on the mandible of a patient.

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Likewise, unless otherwise noted, any steps described herein are not limited to a particular order, such that steps may be rearranged in some instances to achieve the same or substantially similar result.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to directions, such as "forward," "rearward," "upper," "lower," "left," "right," etc. These references, and other similar directional references in the present application, are only to assist in helping describe and to understand the particular embodiment and are not intended to limit the present disclosure to these directions or locations.

The following discussion provides examples of methods and orthodontic apparatuses that include a screw device for stretching or contracting a patient's dental arches sideward or inward horizontally, expanding the lower jaw bone, as well as enlarging the oral cavity and upper pharyngeal airway. This expander design gives the clinician the ability to direct expansion or constriction forces to various segments of the lower dental arches in nonparallel configuration.

One purpose of the apparatuses described herein is to provide an expansion and constriction screw apparatus which can be used in multipurpose manner to not only expand the front and back teeth and sections of the lower jaw and oral cavity in nonparallel ways in transverse directions, respectively, but also to effectively constrict the mandibular dental arch front and back teeth.

This purpose is achieved, in some embodiments, by connecting respective ends of rods rotatable head members with a threaded hole where the threads of the threaded holes are of opposite hand on each side, and by providing a twin screw on respective ends of the rods which is in threaded engagement with the threaded holes of the rotatable head members attached to the each ends of the rods. The twin screw assembly of this design makes it possible to exert independent, nonparallel, transverse expansion and constriction forces on the front and/or back teeth.

In some embodiments, the adjustable twin screw assemblies are embedded in mirror image extension plates, the separate parts of which are formed to fit against teeth and supporting soft palate on opposite sides of the lower jaw, with the plates being separated sufficiently to enable the twin screw assemblies to fit between them and to thereby adjust the relative positions of the two plate parts.

Figure 2:
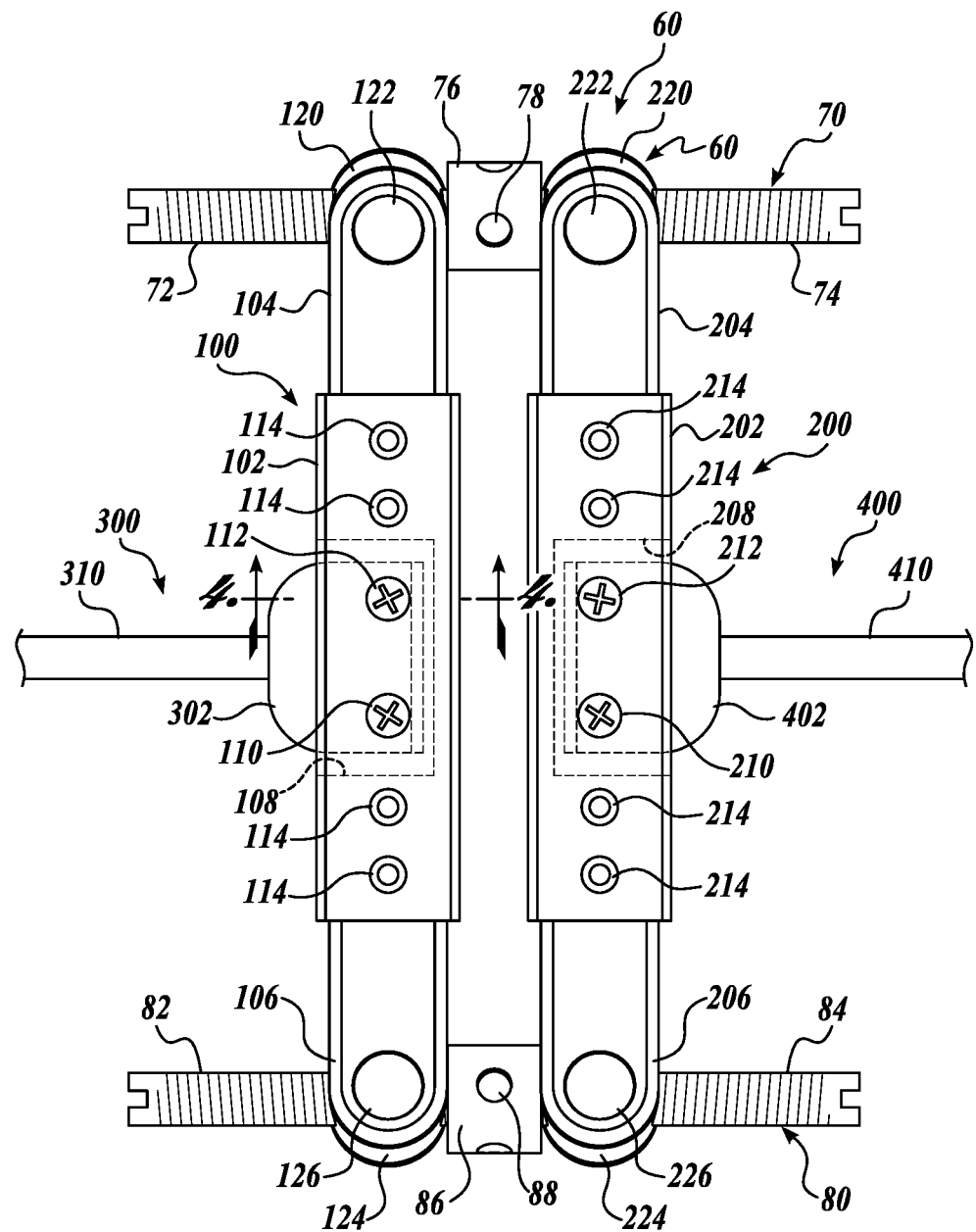
FIG. 2 shows a partial top view of the distractor of FIG. 1.
Figure 3:
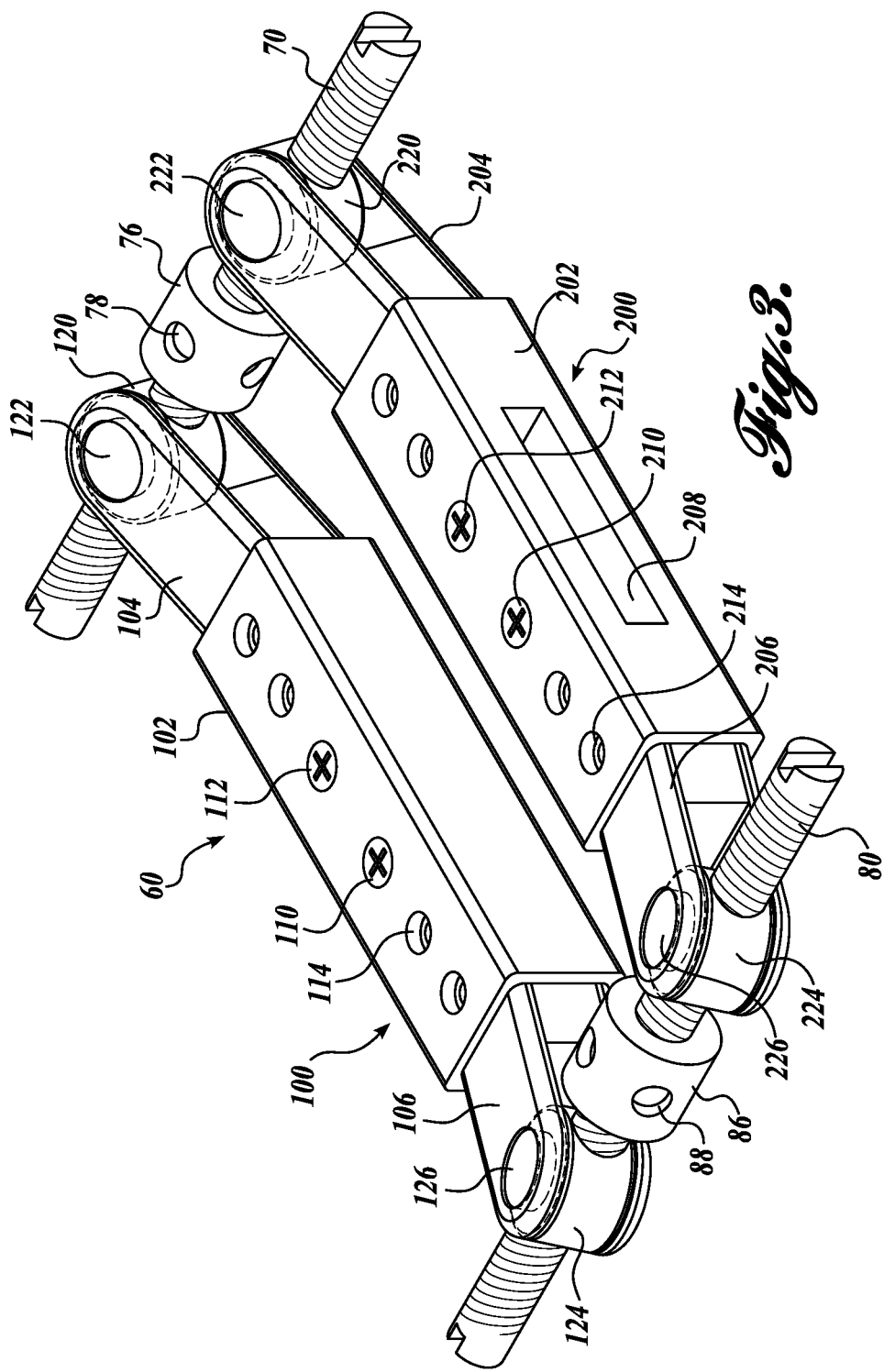
FIG. 3 show an isometric view of a screw assembly of the distractor of FIG. 1.

Referring to FIGS. 1-5, a first embodiment of a mandibular distractor 50 will now be described. The distractor includes a screw assembly 60 that is coupled to one or more lower teeth and/or mandibular bones of a patient by a pair of coupling assemblies 300, 400. As best shown in FIGS. 2 and 3, the screw assembly includes a first rod 100 and a second rod 200 coupled to each other by a first screw 70 and a second screw 80. In the illustrated embodiment the second rod 200 is a mirror image of the first rod 100. For the sake of brevity, the first rod 100 will be described herein with the understanding that the second rod 200 is similar to the first rod, and a component of the second rod with a reference number 2XX corresponds to a similar component 1XX of the first rod.

The first rod 100 includes a central body section 100 with a first clevis 104 disposed at a first end, and a second clevis 106 disposed at a second end. The first and second devises 104 and 106 are illustrated as being integrally formed with the central body section 100; however, embodiments are contemplated in which the devises are formed separate from the central body section and then attached by known fasteners, adhesives, or other means. Further embodiments are contemplated in which the distance between the devises 104 and 106 is adjustable. In this regard, one or both devises 104 and 106 can be configured to slidingly engage the central body section 100 and then selectively positioned and secured in place. This and other embodiments that enable adjustment of the clevis positions are contemplated and should be considered within the scope of the present disclosure.

A first rotatable head member 120 is positioned between the arms of the first clevis 104. Trunnions 122 extend from opposing sides of the first rotatable head member 120, and each trunnion is received within a hole formed in one of the arms of the first clevis 104. In this manner, the first rotatable head member 120 is rotatably mounted to the first clevis 104 about an axis that passes through the center of the trunnions 122. At the other end of the rod 100, a second rotatable head member 124 has trunnions 126 extending from opposite sides to rotatably mount the second rotatable head member to the second clevis 106 in a manner similar to the mounting of the first rotatable head member 120 to the first clevis 104. Each of the rotatable head members 120 and 124 is respectively provided with threaded to threadedly engage the first end 72 and 82 of first and second twin screws 70 and 80, respectively.

The first twin screw 70 has a first end 72 with threads formed thereon. The first end 72 of the first twin screw 70 threadedly engages the threaded hole formed in the first rotatable head member 120 of the first rod 100. A second end 74 of the first twin screw 70 also has threads formed thereon, wherein the threads of the first end 72 are of the opposite hand of the threads of the second end. The second end 74 first twin screw 70 is threadedly engaged with the threaded hole formed in first rotatable head member 220 of the second rod 200. Thus, rotation of the first twin screw 70 in a first direction moves the first rotatable head members 120 and 220, and therefore, the first ends of the first and second rods 100 and 200, away from each other. Conversely, rotation of the first twin screw 70 in a second direction moves the first a rotatable head members 120 and 220, and therefore, the first ends of the first and second rods 100 and 200, towards each other.

The middle portion of the first twin screw 70 includes a fitting 76 provided with two through-and-through openings 78 positioned perpendicular to each other 8a and 8b. The first twin screw 70 can be rotated by means of a tool inserted into one of the crossed openings 70. Other possible embodiments of the fitting 76 include flats formed on the fitting to allow a wrench to engage the flats to facilitate rotation of the first twin screw 70. These and other features that enable rotation of the first twin screw 70 are contemplated and should be considered within the scope of the present disclosure.

The second twin screw 80 is similar to the first twin screw 70, having first and second ends 82 and 84 that are threaded so that the threads of one end are of the opposite hand of the threads of the other end. The threaded ends 82 and 84 threadedly engage the second rotatable head members 124 and 224, respectively, so that rotation of the second twin screw 80 in a first direction moves the second rotatable head members 124 and 224, and therefore, the second ends of the first and second rods 100 and 200, away from each other. Conversely, rotation of the second twin screw 80 in a second direction moves the second rotatable head members 124 and 224, and therefore, the second ends of the first and second rods 100 and 200, towards each other.

Figure 4:
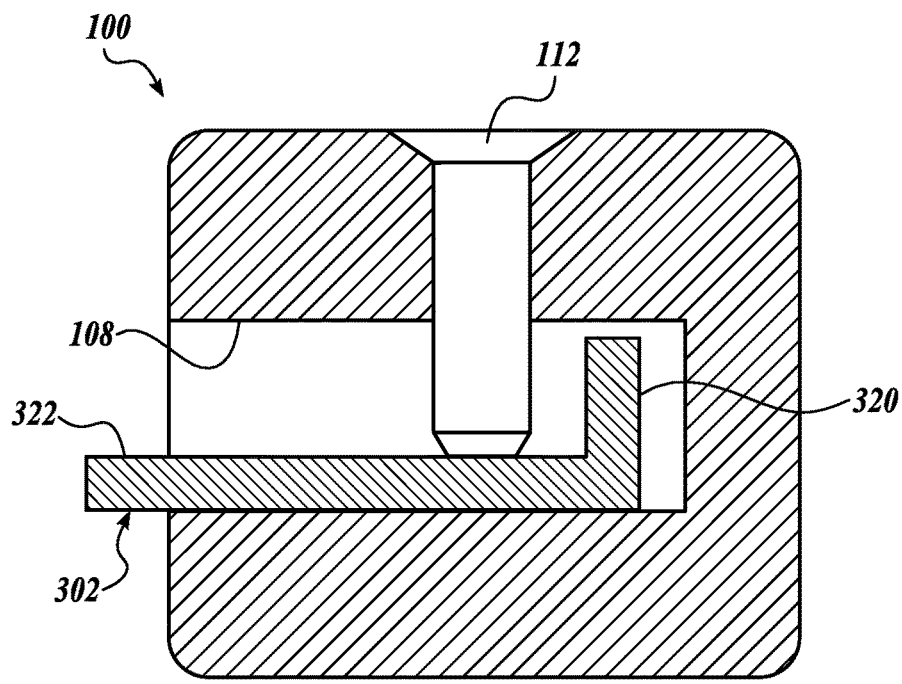
FIG. 4 shows a partial cross-sectional view of the screw assembly of FIG. 3.
Figure 5:
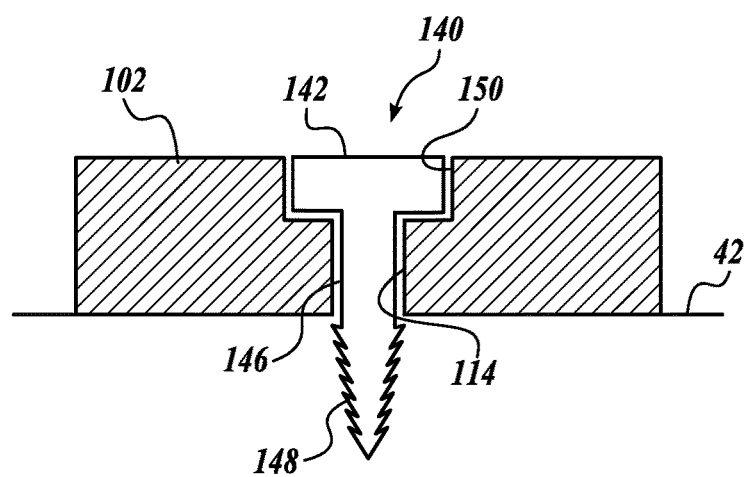
FIG. 5 shows a second partial cross-sectional view of the screw assembly of FIG. 3.

Referring now to FIGS. 1, 2, and 4, a first coupling assembly 300 couples the first rod 100 to the lower right premolar 22. The first coupling assembly 300 includes a base 302 that has an L-shaped cross section. The base 302 is sized to fit within the slot 108 formed in the body 102 of the first rod 100. Set screws 110 and 112 extend from an outside surface of the body 102 into the cavity 108. As best shown in FIG. 4, the set screws engage a flat portion 322 of the base 302 to press the base against one side of the slot 108, thereby maintaining the position of the base, and therefore, the coupling assembly 300, relative to the first rod 100. A leg 230 of the base extends away from the flat portion 322 and is positioned so that the leg will engage the set screws 110 and 112 to prevent the base from disengaging with the first rod 100 unless the set screws are first loosened or removed.

Referring back to FIG. 1, the coupling assembly 300 includes an extension arm 310 extending outward from the base 302. A premolar band 312 is coupled to the extension arm 310 and is sized and configured to be fitted on the premolar 22. With the premolar band 312 secured to the premolar 22, the first rod is fixedly secured to one side of the mouth of the patient.

In the illustrated embodiment, the second coupling assembly 400 is a mirror image of the first coupling assembly, wherein a component of the second coupling assembly having a reference number of 4XX corresponds to a component from the first coupling assembly 300 having a reference number of 3XX. It will be appreciated that the disclosed coupling assemblies are exemplary only and should not be considered limiting. In this regard, various other embodiments are contemplated, wherein different configurations are provided to couple the screw assembly 60 to the patients teeth, mandibular bones, or a combination thereof. Moreover, various configurations are contemplated in which one coupling assembly is not a mirror image of the other coupling assembly, for example, if a patient is missing one or more teeth or has other oral asymmetries.

The use of the slotted configuration to couple base 302 to the first rod 100 allows for adjustment of the coupling assemblies 300 and 400 relative to the screw assembly 60. That is, the coupling members 300 and 400 can be located relative to the teeth/mandibular bones, and then the set screws can be tightened to lock the position of the coupling assemblies to the screw assembly 60. The adjustability of the coupling members 300 and 400 in combination with the nonparallel expansion capability makes the screw assembly 60 provides a distractor that is easily adjustable to the patient. The appliance does not need to be pre-adjusted, but can be adjusted by a clinician right after the opening the packaging. Also, such a device does not require prefabrication.

Figure 11:
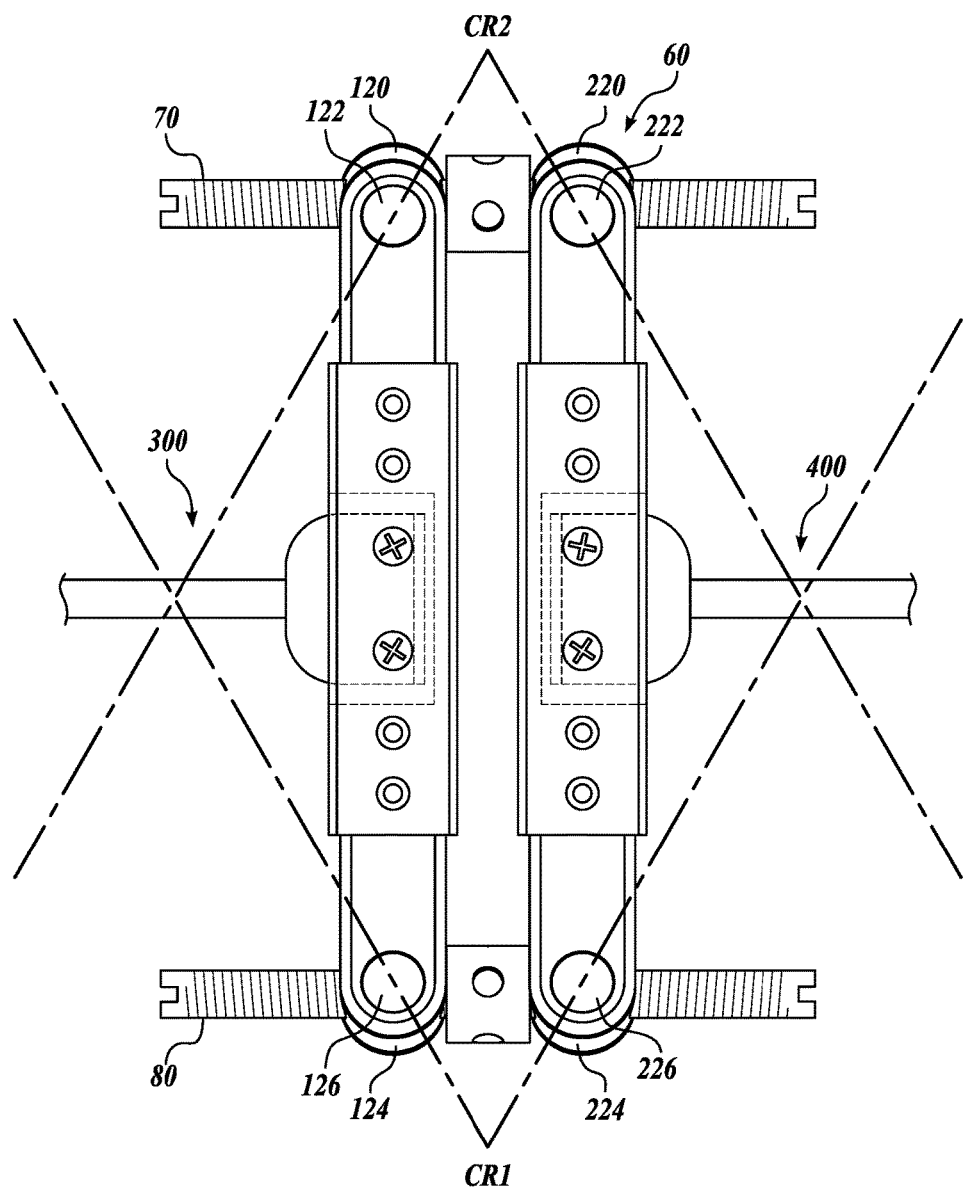
FIG. 11 shows a top view of the screw assembly of FIG. 3 with the directions of forces which may be exerted on the teeth and different areas of the lower jaw and airway by the distractor and around the centers of rotation.

An advantage of embodiments of the dual expander design type screw and orthodontic appliance assembly is that it is possible to select any desired variation of transverse extension and/or constriction at the front and back teeth using one appliance. FIG. 11 shows the directions of forces which may be exerted on the teeth and different areas of the lower jaw and airway and around the centers of rotation CR1, CR2 of the screw assembly 60. Transverse expansion force (TE) and transverse contraction force (TC) are achieved by rotating the first and second twin screws 70 and 80 by equal amounts, thereby maintaining the angular position of the first and second rods 100 and 200 relative to each other. Rotational forces R1 and R2 are achieved turning the first twin screw 70 and the second twin screw 80 asymmetrically so that the angular position of the first and second rods 100 and 200 changes relative to each other.

Figure 6:
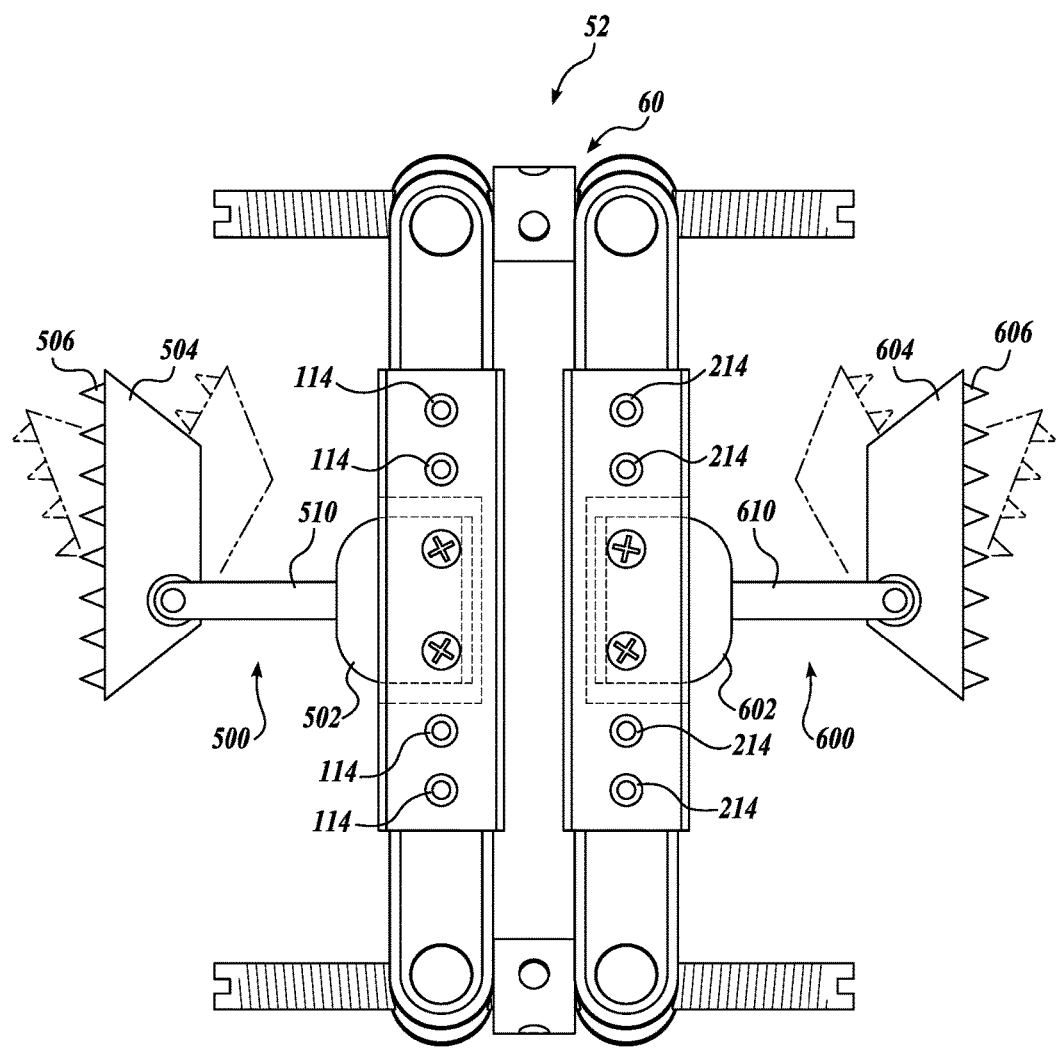
FIG. 6 shows a top view of a mandibular distractor according to a second representative embodiment of the present disclosure.
Figure 7:
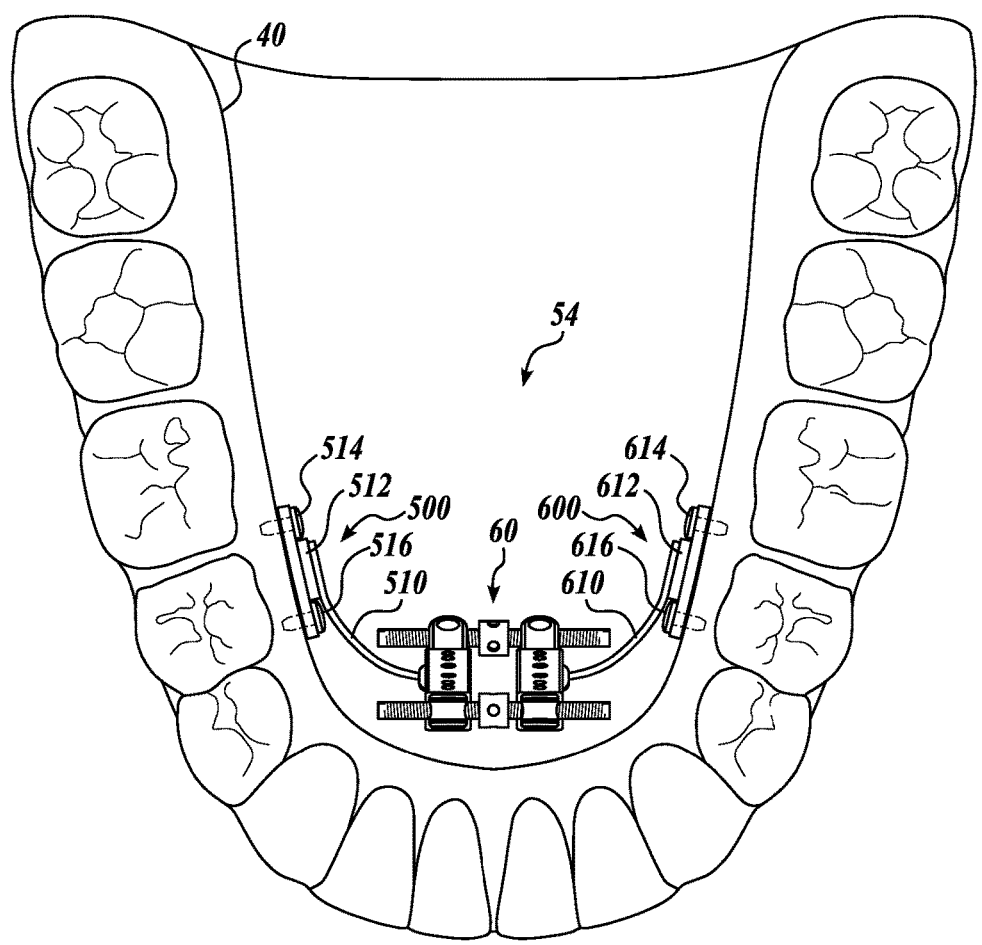
FIG. 7 shows a top view of the mandibular distractor of FIG. 6, wherein the mandibular distractor is installed on the mandible of a patient.

FIGS. 6 and 7 show a second representative embodiment of a mandibular distractor 52 according to the present disclosure. The distractor 52 includes screw assembly 60 as previously described. Coupling assemblies 500 and 600 attached the screw assembly 60 to the mouth of the patient. In the illustrated embodiment, the second coupling assembly 600 is a mirror image of the first coupling assembly 500, wherein a component of the second coupling assembly having a reference number of 6XX corresponds to a component from the first coupling assembly 500 having a reference number of 5XX. The first coupling assembly 500 will be described herein with the understanding that unless otherwise noted, the second coupling assembly 600 is a mirror image of the first coupling assembly.

As shown in FIG. 6, the first coupling assembly 500 is similar to previously described first coupling assembly 300, having a base 502, and an extension arm 510 extending therefrom. A bone-borne plate 504 is rotatably coupled to the extension arm 510 and has a plurality of insertion studs 506 disposed on the outer surface of the bone-borne plate for securing and attaching the plate in a patient's mandible bones bilaterally. FIG. 7 shows a variation of the embodiment of FIG. 6 in which fasteners 512 and 516 are used in addition to or in lieu of the insertion studs 510 to secure the plate 512 to the patient's bones.

This bone-borne option can eliminate the need of orthodontic bands on molars and premolars and is an effective system for children at early mixed dentition with primary teeth or missing teeth in transitional stage of dental development who have lower jaw and arch constriction, excessive lower arch expansion, cross bite (unilateral/bilateral), and/or severe upper airway constriction. This bone-borne embodiment may need surgical intervention for insertion of the appliance into the patient's mouth under sedation and local anesthesia. In some embodiments, the screw holes 214 FIG. 3 will be used as main attachment of the expander to the lower jaw at the osteotomy site of the patient's mouth with no other means for attachment to the teeth in cases that patient is partially or fully edentulous with no teeth or teeth that cannot support the force of applied forces from expansion or distraction.

Figure 8:
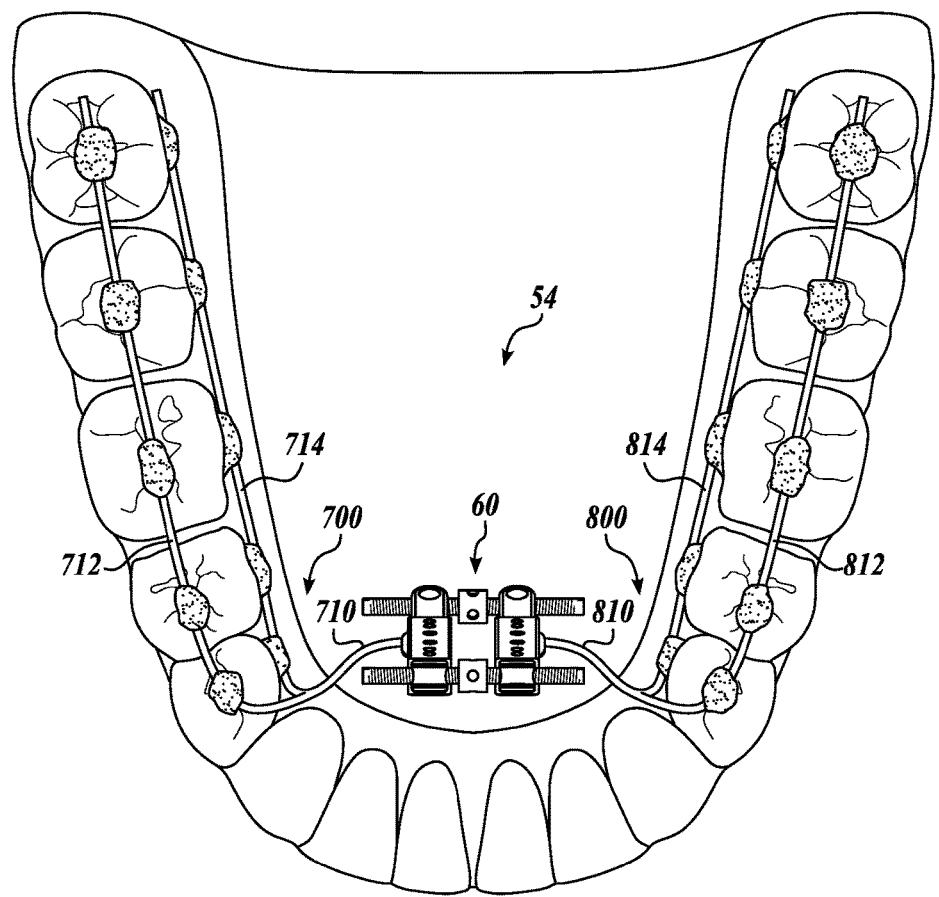
FIG. 8 shows a top view of a mandibular distractor according to a third representative embodiment of the present disclosure, wherein the mandibular distractor is installed on the mandible of a patient.

FIG. 8 shows a third representative embodiment of a mandibular distractor 54 according to the present disclosure. The distractor includes screw assembly 60 as previously described. Coupling assemblies 700 and 800 attached the screw assembly 60 to the mouth of the patient. In the illustrated embodiment, the second coupling assembly 800 is a mirror image of the first coupling assembly 700, wherein a component of the second coupling assembly having a reference number of 8XX corresponds to a component from the first coupling assembly 700 having a reference number of 7XX. The first coupling assembly 700 will be described herein with the understanding that unless otherwise noted, the second coupling assembly 800 is a mirror image of the first coupling assembly.

As shown in FIG. 8, the first coupling assembly 700 is similar to previously described first coupling assembly 300, having a base 702 and an extension arm 710 extending therefrom. The extension arm splits into an occlusal portion 712 and a lingual portion 714. The occlusal portion 712 is bonded to the occlusal side of one or more teeth using adhesive cement or other suitable means. The lingual portion 714 is bonded to the lingual side of one or more teeth using adhesive cement or other suitable means.

Alternate embodiments are contemplated in which various combinations of bands, rest arms, and bonded wires are utilized. For example, molar bands and bicuspid bands can be utilized. In addition, occlusal and lingual rest arms and bands can be secured to various teeth using adhesive cement or other suitable means. These and other configurations for securing appliances to teeth, both alone or in combination with each other, are contemplated and should be considered within the scope of the present disclosure.

Figure 9:
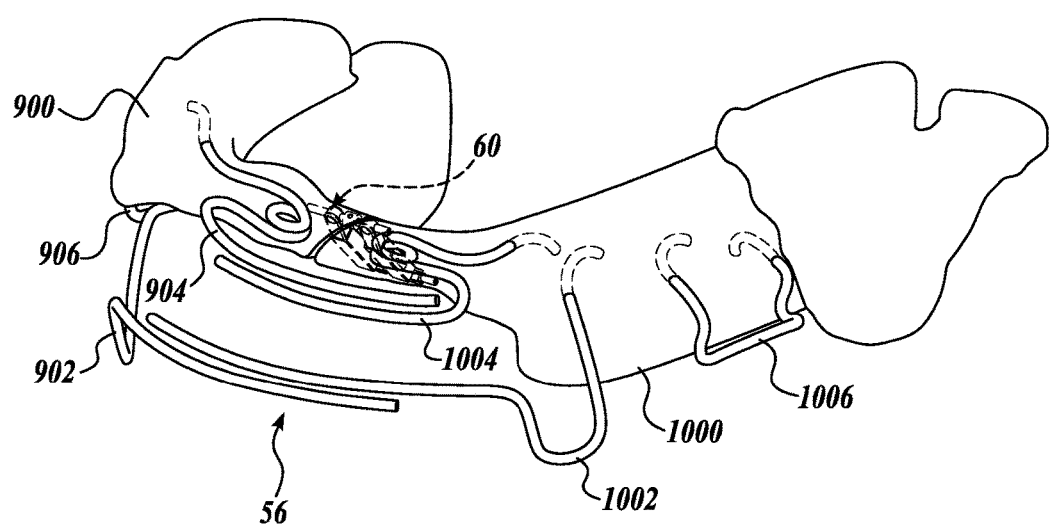
FIG. 9 shows an isometric view of a mandibular dental arch according to a fourth representative embodiment of the present disclosure.
Figure 10:
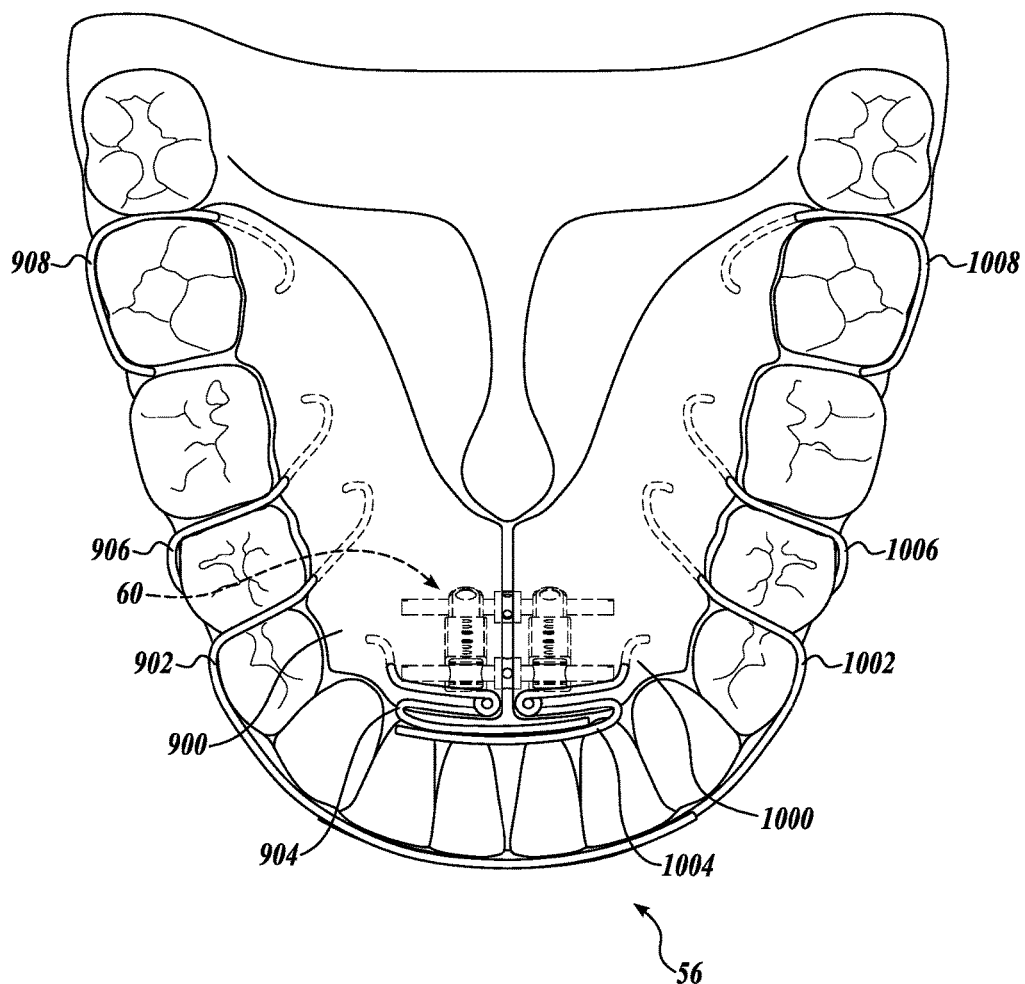
FIG. 10 shows a top view of the mandibular dental arch of FIG. 9.

Referring to FIGS. 9 and 10, a fourth representative embodiment in the form of a removable mandibular distractor 56 is shown. The distractor 56 includes a first mandibular plate 900 coupled to a second mandibular plate 1000 by the previously described screw assembly 60. In the illustrated embodiment, the second mandibular plate 1000 is a mirror image of the first mandibular plate 900, wherein a component of the second mandibular plate having a reference number of 10XX corresponds to a component from the first mandibular plate 900 having a reference number of 9XX. The first mandibular plate 900 will be described herein with the understanding that unless otherwise noted, the second mandibular plate 1000 is a mirror image of the first mandibular plate.

The first mandibular plate 900 is formed of acrylic or other suitable material and is preferably formed from a mold of the patient's maxillary dental arch. A plurality of posts 906 and 908 are molded into the mandibular plate 900 and extend therefrom to engage the patient's teeth when distractor 1100 is installed. The first mandibular plate also includes first and elongate aligning arms 902 and 904, respectively, extending from a forward portion of the mandibular plate 900. The first aligning arm 902 is configured such that when the distractor 56 is installed, the first aligning arm is positioned adjacent to and extends along the labial portion of one or more anterior teeth. The second aligning arm 904 is configured such that when the distractor 56 is installed, the second aligning arm is positioned adjacent to and extends along the lingual portion of one or more anterior teeth.

Referring to FIG. 10, with the distractor 56 installed, the posterior teeth are disposed between the sides of the mandibular plates 900 and 1000 and the posts 906, 908, 1006 and 1008 as retention means extending therefrom. The anterior teeth are positioned between the first aligning arms 902 and 1002 and the second aligning arms 904 and 1004. The position of the mandibular plates 900 and 1000 relative to each other is selectively adjustable using the screw assembly 60, a portion of which is embedded in or attached to each mandibular plate. In this manner, the distractor 56 can be expanded or contracted, both symmetrically or asymmetrically with respect to the front and back portions. As the distractor 56 is expanded and contracted, the position of the teeth relative to the distractor is maintained by the posts and aligning arms. Further, in contrast to previous embodiments, the distractor 56 is easily removed and installed by the patient.

Alternate embodiments of the distractor 56 of FIGS. 9 and 10 are contemplated wherein the shape of the mandibular plates 900 and 1000 varies. For example, the mandibular plates can extend over the occlusal surface of the front or back teeth, or both, bilaterally or unilaterally, to create bite ramps.

The following is a protocol of alternate rapid mandibular expansion and slow constrictions (Alt-RMESC). The Alt-RMESC protocol was developed for the growth modification and treatment of constricted mandible in class I, class II, or class III type skeletal discrepancies not only for the growing patients but also for non-growing patients. The clinical devices and protocol are exactly the same for both groups of patients. The devices are the different embodiments of dual expanding mandibular distractor.

The complete Alt-RMESC protocol involves 4-6 months. The expanded space between the adjacent teeth to the osteotomy site could be saved for relieving anterior crowding, for compensating dental effects (e.g., the proclined mandibular incisors), for correction of facial asymmetries, for expansion of the base of the tongue, or for expansion of the oral cavity and upper airway.

The HYRAX or bone-born type expanders cannot be as effective as embodiments of the dual expanding mandibular distractor described herein for the expanding the osteotomy site under the Alt-RMESC protocol due to their parallel expansion effect. The HYRAX or bone-born type expanders displace the condyles laterally. Not only do the embodiments of the dual expanding mandibular distractor described herein provide differential nonparallel expansion capability, but also permit the Alt-RMESC protocol described herein. Anchoring the mandibular expander device to the bicuspid teeth by rounded roots makes the expansion efficient without lateral displacement of the condyles since the expansion in the two halves of the mandible around the vertical access of each condyle will be compensated by the mesial rotation of the bicuspid teeth in their respective sockets.

Several types of rapid mandibular expanders have been used for the purpose of mandibular expansion. They include the HYRAX and bone-born type expanders. These appliances expand the mandible outward in a parallel manner.

Embodiments of the dual mandibular expander described herein are developed for incremental, differential, nonparallel expansion and constriction of anterior and posterior mandible. In some embodiments, dual expanding mandibular distractors have two identical rotation hinges. The hinges permit expansion and rotation of each half of the mandible outward and inward, sequentially in nonparallel increments through the two independent axes of rotation. In one embodiment, one axis of rotation is close to the floor of the mouth and the other axis of rotation is lingual to the incisor teeth. This model of expansion entails lateral rotation of mandibular halves around the vertical excess of each condyle with a lower chance of condylar resorption or lateral displacement. It has been verified in an experimental study that the HYRAX or bone-born expanders significantly displaced the condyles laterally. Therefore, in terms of expanding the mandible avoiding the lateral displacement of the condyles, the embodiments of dual expanding mandibular distractors described herein are superior to the other types of expanders for the treatment of a hypoplastic or transversely deficient mandible in growing or non-growing patients.

The osteotomy site is an osteogenic and osteolytic tissue site that allowed for a certain degree of expansion. Within the biological and physiological limitations, expansion of osteotomy site leads to bone formation. This phenomenon also has been referred as the sutural distraction osteogenesis that resembles the callus distraction osteogenesis in the long bone. For the callus distraction osteogenesis in long bone, it has been suggested that the optimal (biological and physiological) rate of distraction is 1 mm/day, so in this protocol it is recommended between 0.5 to maximum 1 mm of expansion in front every day until the full overcorrection is achieved. It also has been considered that 1 mm/day is the biological, physiological, and optimal rate for rapid mandibular osteotomy site expansion. In one embodiment, the optimal rate of expansion or distraction for any osteogenetic tissue, such as suture or callus, is 1 mm/day. To encourage the proper biologic bone formation at the expanded osteotomy site right after the surgery, a sequence including a lag phase, a distraction phase, and a consolidation phase is recommended.

In the lag phase, before proceeding with distraction, there is a variable period (latency period) to allow for initial bone formation to occur. In one embodiment, the period is typically 3-5 days. However, in other embodiments, such as in growing patients, the latency period may last only 24 to 48 hours or be omitted entirely. In yet other embodiments, with skeletal maturity, the latency period is typically 5-7 days in non-growing patients.

In the distraction phase, the process of distraction is activated when bone segments are gradually expanded apart by an expansion device. In one embodiment, three variables are set: the rate of distraction, the rhythm or frequency of distraction, and the total time of distraction. In one embodiment, the rate of distraction is typically 1.0 mm/day. In other embodiments, the rate can vary up to 2.0 mm/day in younger children to avoid early consolidation and down to 0.25-0.5 mm/day in older patients. In one embodiment, this is divided throughout the day every 6 to 12 hours, determining the rhythm or frequency of distraction. While the distraction rate may be 1.0 mm/day, in one embodiment, the tissues are maintained under constant tension by dividing the total daily rate of distraction into smaller increments throughout the day to favor histogenesis.

In one embodiment, the total time of the distraction phase is customized to the severity of the mandibular constriction. In other embodiments, other factors may be taken into account to determine the total time of the distraction phase.

In the consolidation phase, once the desired correction is achieved in the distraction phase, mineralization of the immature bone is allowed to occur. In one embodiment, the distractor is locked into place to maintain stability until the newly formed bone has sufficient strength. The length of this phase varies depending on the circumstances. In some embodiments, 6-8 weeks may be an adequate length of the consolidation phase. In one embodiment, the end of the consolidation phase is determined based on periodic panoramic and/or CBCT radiographs.

Following the consolidation phase, constriction of the mandibular teeth can be performed. In one embodiment, constriction is performed at a rate of one turn two days per week, equaling 0.5 mm constriction of the mandibular teeth per week until a particular tongue/arch width ratio is acquired. In some embodiments, this protocol will reduce the chance of bone resorption as result of osteolysis at the osteotomy site which can impact negatively the transverse dimension of the oral cavity. In some examples, the daily expansion of the osteotomy site is biologically and physiologically confined within less than 1 mm/day or constriction of less than 0.5 mm/week. The slow constriction eliminates the constriction of the body of the mandible.

In an alternative protocol, the stem cells of the patient can be collected from the blood or bone marrow or in combination with platelet rich plasma injected in the area of distracted bone and surgical site to enhance or facilitate the amount of expansion and shorten the period of stabilization and ossification. Periodic panoramic or cone beam computed tomography taken at monthly intervals indicates that the distraction gaps are bridged by new bony regenerate.

This stage of protocol provides significant expansion in the body of the mandible at the base of the tongue for proper airway expansion. It also widens the mandibular area to overcome narrow dentoalveolar structures. The over-expansion at the alveolar area enables the next stage of protocol for improvement of recessed gingival areas. The apparatus is activated by slow reverse contraction of 2 turns weekly to constrict the posterior teeth to the final desired width, and embed the teeth back to the newly-formed alveolar bone. In the next stage, a non-extraction orthodontic alignment of the mandibular teeth can be accomplished. This technique and apparatus provide an efficient technique to avoid extraction of the teeth for relieving crowding and can develop an adequate recipient site for insertion of implants to replace the missing teeth and as simple surgical alternatives, can be an excellent adjunct for treatment of obstructive sleep apnea. It can be utilized for correction of facial deformities caused by mandibular or chin transverse, vertical and sagittal deficiencies. This technique by elongating the body of the mandible can contribute to the sagittal elongation as well as transverse expansion of the body of the mandible symmetrically when the osteotomy site is placed between the lower centeral incisors or asymmetrically when osteotomy site is extending distally toward the back of the mouth.

Figure 12:
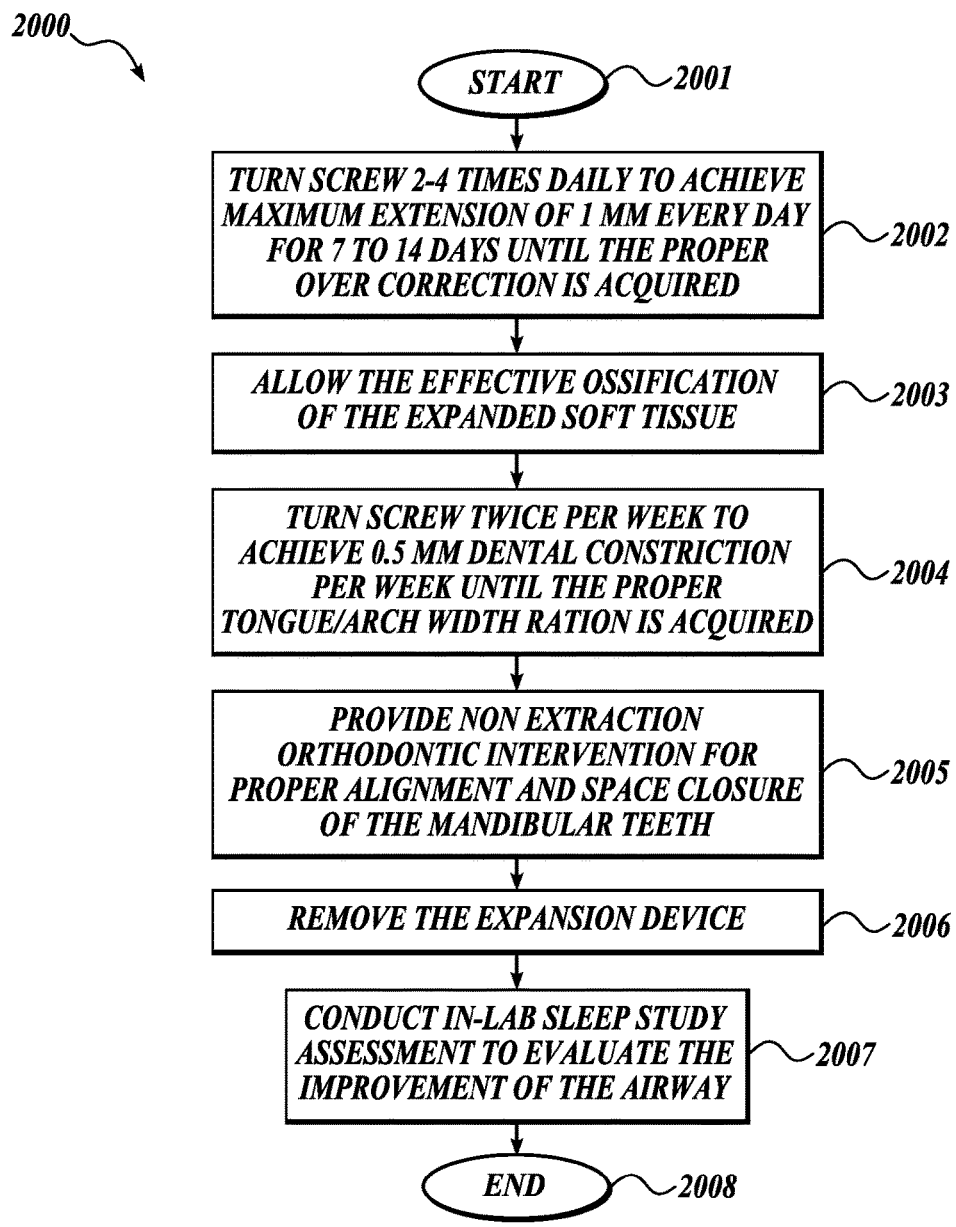
FIG. 12 shows a method of treating a patient using a mandibular distractor.

FIG. 12 shows an exemplary process 2000 of applying an Alt-RMESC protocol with total treatment period of 4-6 months. The process 2000 starts at step 2001 and proceeds to step 2002, wherein the screw is turned 2-4 times daily to provide a maximum extension of 1 mm every day for 7 to 14 days until the proper over correction is acquired.

The process proceeds to step 2003, during which approximately 2 months of consolidation are provided to allow the effective ossification of the expanded soft tissue. Meanwhile, the teeth in front of anchored teeth for the appliance are allowed to freely move toward the distraction site.

Next, in step 2004, the screw is turned approximately one rotation twice per week to provide approximately 0.5 mm dental constriction per week until the proper tongue/arch width ratio is acquired.

In step 2005, post expansion non extraction orthodontic intervention is provided to achieve proper alignment and space closure of the mandibular teeth.

Next, in step 2006, the expansion device is removed.

Finally, in step 2007, a frontal view cephalometric radiographic assessment of the nasal cavity expansion after each rapid expansion period is performed.

While various embodiments have been illustrated and described, it will be appreciated that various changes can be made therein without departing from the spirit and scope of the claimed subject matter.

The embodiments of the invention in which an exclusive property or privilege is claimed are defined as follows:

1. An orthodontic assembly comprising a screw system, the assembly capable of expansion or constriction to adjust the position of one or more of a patient's lower teeth, jaws, oral cavity, or airway, and the screw system comprising:

a first rod and a second rod, wherein each of the first and second rods has a first end and a second end;

wherein said first and second rods are adjacent and comprise a system further including a mechanism that permits said first ends of said first and second rods to be either spread apart or drawn together independently of said second ends of said first and second rods, which can be either spread apart or drawn together independently of said first ends of said first and second rods;

extension arms coupled to said first and second rods, and wherein a bicuspid band is rigidly affixed to each said arm, each said bicuspid band being configured to be secured around a mandibular bicuspid tooth of a patient, thereby permitting said bicuspid teeth to which said bands are affixed to be moved outwardly and rotated slightly in their sockets, thereby spreading apart a pair of mandible halves and causing said mandible halves to rotate about the condyles; and wherein said mechanism includes:

(a) a plurality of rotatable head members each of which comprises a threaded hole, wherein the plurality of rotatable head members comprises a first rotatable head member connected to the first end of the first rod, a second rotatable head member connected to the first end of the second rod, a third rotatable head member connected to the second end of the first rod, and a fourth rotatable head member connected to the second end of the second rod, wherein the threaded holes of the first and second rotatable head members are of opposite hand, and wherein the threaded holes of the third and fourth rotatable head members are of opposite hand;

(b) a first twin screw having threaded ends of opposite hand, wherein the threaded ends of the first twin screw are configured to engage the threaded holes of the first and second rotatable head members such that rotation of the first twin screw causes the first and second rotatable head members to either drawn together or spread apart, and the first ends of the first and second rods to either drawn together or spread apart; and (c) a second twin screw having threaded ends of opposite hand, wherein the threaded ends of the second twin screw are configured to engage the threaded holes of the third and fourth rotatable head members such that rotation of the second twin screw causes the third and fourth rotatable head members to either drawn together or spread apart, and the second ends of the first and second rods to either drawn together or spread apart.

2. A method of treating the mandible of a patient using a mandibular distractor, wherein the mandibular distractor comprises at least two independent axes of rotation and is capable of nonparallel distraction and further including extension rods terminating in and rigidly affixed to bicuspid bands, the method comprising:

splitting the mandible in two, at the front center, thereby creating mandible-halves, each mandible-half being hinged at a condyle;

attaching said bicuspid bands to a bicuspid on either side of the mouth;

expanding said distractor so that said extension rods press outwardly on said bicuspid bands, and wherein said bicuspid bands retain an original orientation relative to said extension rods, thereby causing the bicuspids to which said bicuspid bands are attached to rotate relative to their sockets as said mandible-halves rotate outwardly about said condyles.

3. The method of claim 2, wherein the method ends in a final state that is based on a particular tongue/arch width ratio.

4. The method of claim 2, wherein said mandible halves are separated at a rate that is greater than 0.25 mm per day.

5. The method of claim 2, wherein said mandible halves are separated until they are in a state of overcorrection.

6. The method of claim 5, wherein said mandible halves are permitted to consolidate for a period of time, after said separation, by maintaining a current expanded position of the mandible for said period of time by the mandibular distractor.

7. The method of claim 6, wherein said mandible halves are pulled into constriction after said period of consolidation, by adjusting said mandibular distractor so that said bicuspid bands now pull inwardly on said bicuspids.

\* \* \* \* \*